US012589125B2

(12) United States Patent
Chen et al.

(10) Patent No.: US 12,589,125 B2
(45) Date of Patent: Mar. 31, 2026

(54) YOGURT FOR REGULATING INTESTINAL TRACT, PREPARATION METHOD THEREFOR, AND USE THEREOF

(71) Applicant: Beijing Sanyuan Foods Co., Ltd., Beijing (CN)

(72) Inventors: Lijun Chen, Beijing (CN); Yanpin Liu, Beijing (CN); Jiantao Li, Beijing (CN); Junying Zhao, Beijing (CN); Bin Liu, Beijing (CN); Lu Liu, Beijing (CN); Weicang Qiao, Beijing (CN); Weiming Zhou, Beijing (CN)

(73) Assignee: BEIJING SANYUAN FOODS CO., LTD., Beijing (CN)

( * ) Notice: Subject to any disclaimer, the term of this patent is extended or adjusted under 35 U.S.C. 154(b) by 340 days.

(21) Appl. No.: 18/175,330

(22) Filed: Feb. 27, 2023

(65) Prior Publication Data

US 2023/0210924 A1 Jul. 6, 2023

Related U.S. Application Data

(63) Continuation of application No. PCT/CN2020/118396, filed on Sep. 28, 2020.

(51) Int. Cl.
| | |
|---|---|
| *A61K 35/747* | (2015.01) |
| *A23C 9/123* | (2006.01) |
| *A23C 9/13* | (2006.01) |
| *A61K 9/00* | (2006.01) |
| *A61K 35/744* | (2015.01) |
| *A61K 35/745* | (2015.01) |
| *A61K 47/46* | (2006.01) |
| *A61P 1/10* | (2006.01) |

(52) U.S. Cl.
CPC .......... *A61K 35/747* (2013.01); *A23C 9/1234* (2013.01); *A23C 9/1307* (2013.01); *A61K 9/0056* (2013.01); *A61K 35/744* (2013.01); *A61K 35/745* (2013.01); *A61K 47/46* (2013.01); *A61P 1/10* (2018.01); *A23V 2400/113* (2023.08); *A23V 2400/123* (2023.08); *A23V 2400/145* (2023.08); *A23V 2400/165* (2023.08); *A23V 2400/169* (2023.08); *A23V 2400/249* (2023.08); *A23V 2400/519* (2023.08); *A23V 2400/531* (2023.08); *A23V 2400/533* (2023.08)

(58) Field of Classification Search
CPC .. A61K 35/747; A61K 35/745; A61K 35/744; A23V 2400/113; A23V 2400/123; A23V 2400/145; A23V 2400/165; A23V 2400/169; A23V 2400/246; A23V 2400/519; A23V 2400/531; A23V 2400/533
See application file for complete search history.

(56) References Cited

U.S. PATENT DOCUMENTS

| | | | |
|---|---|---|---|
| 2017/0165303 A1 | 6/2017 | Olmstead | |
| 2021/0068414 A1* | 3/2021 | Takahashi | ................. A61P 3/02 |

FOREIGN PATENT DOCUMENTS

| | | |
|---|---|---|
| CN | 105532869 A | 5/2016 |
| CN | 111011495 A | 4/2020 |
| CN | 111387288 A | 7/2020 |

OTHER PUBLICATIONS

CN 111387288 A, English Translation (Year: 2020).*
Australian Examination report No. 1 issued in related Australian patent application No. 2020469798; mailed Aug. 12, 2022; 7 pgs.
First Office Action issued in related Chinese patent application No. 202011042108.9; mailed Oct. 13, 2021; 17 pgs.
International Search Report issued in International Application No. PCT/CN2020/118396; mailed Jun. 11, 2021; 7 pgs.
Notification of Acceptance (Receipt) Viability Report; Deposit of biological material for patent procedures; China General Microbiological Culture Collection Center (CGMCC); CGMCC No. 19749; Institute of Microbiology, CAS; Beijing, China; issued Apr. 27, 2020; 2 pgs.
Notification of Acceptance (Receipt) Viability Report; Deposit of biological material for patent procedures; China General Microbiological Culture Collection Center (CGMCC); CGMCC No. 19748 Institute of Microbiology, CAS; Beijing, China; issued Apr. 27, 2020; 2 pgs.
Notification of Acceptance (Receipt) Viability Report; Deposit of biological material for patent procedures; China General Microbiological Culture Collection Center (CGMCC); CGMCC No. 1084 Institute of Microbiology, CAS; Beijing, China; issued Jan. 6, 2004; 2 pgs.

(Continued)

*Primary Examiner* — Ruth A Davis
(74) *Attorney, Agent, or Firm* — HAUPTMAN HAM, LLP

(57) ABSTRACT

Disclosed are a yoghurt for regulating intestinal tract, preparation method therefor, and use thereof, where the yogurt is prepared from raw materials comprising the following parts by weight: 90-97 parts of raw milk, *Lactobacillus gasseri* of $(0.7\text{-}5)\times10^8$ CFU/100 g raw milk, *Streptococcus thermophilus* of $(0.1\text{-}9)\times10^{10}$ CFU/100 g raw milk, *Lactobacillus bulgaricus* of $(0.1\text{-}9)\times10^{10}$ CFU/100 g raw milk, *Lactobacillus acidophilus* of $(0.5\text{-}7)\times10^8$ CFU/100 g raw milk, *Lactobacillus plantarum* of $(0.5\text{-}7)\times10^8$ CFU/100 g raw milk, *Lactobacillus paracasei* of $(0.1\text{-}9)\times10^7$ CFU/100 g raw milk, and other probiotics, and prebiotics such as inulin. The yogurt may regulate the balance of intestinal flora and prevent constipation and gestational diabetes in overweight and/or obese pregnant women during the gestation period.

2 Claims, 2 Drawing Sheets

(56)                     References Cited

OTHER PUBLICATIONS

Notification of Acceptance (Receipt) Viability Report; Deposit of
biological material for patent procedures; China General Microbio-
logical Culture Collection Center (CGMCC); CGMCC No. 1085
Institute of Microbiology, CAS; Beijing, China; issued Jan. 6, 2004;
2 pgs.

* cited by examiner

YOGURT FOR REGULATING INTESTINAL TRACT, PREPARATION METHOD THEREFOR, AND USE THEREOF

RELATED APPLICATIONS

The present application is a Continuation of International Application Number PCT/CN2020/118396 filed Sep. 28, 2020, the disclosure of which is hereby incorporated by reference herein in its entirety.

TECHNICAL FIELD

This disclosure relates to the field of food, and in particular, to a yogurt for regulating intestinal tract, preparation method therefor, and use thereof.

BACKGROUND

In the fast-paced modern society featuring high life pressure, the digestion, metabolism, immunity and other functions of the intestinal tract may be accelerated weaken due to people's bad living habits, which may bring about conditions such as obesity, constipation, indigestion, or even huge health risks. With the upgrading of the concept of intestinal microecological health, the importance of regulating the intestinal microecological balance and improving intestinal health are increasingly noted. For special populations such as pregnant and lying-in women, it is particularly important to regulate intestinal microecology and improve constipation. Constipation and diabetes are common pregnancy complications in overweight and obese pregnant women, which affects pregnancy outcomes to a certain extent. However, there are few drugs available to pregnant women during pregnancy. Therefore, it is important to develop a food that can improve constipation and gestational diabetes by regulating intestinal microecology.

The information disclosed in the background section herein is only intended to enhance the understanding of the general background of this disclosure and should not be taken as an acknowledgement or any form of suggestion that this information forms the prior art already known to a person of ordinary skill in the art.

SUMMARY OF THE INVENTION

Objective

In order to solve the above-mentioned technical problems, the purpose of this disclosure is to provide a yogurt for regulating intestinal tract, preparation method therefor, and use thereof. The yogurt may regulate the balance of intestinal flora and prevent constipation and gestational diabetes in overweight and/or obese pregnant women during the gestation period.

Solution

In order to achieve the object of this disclosure, the embodiments of this disclosure provide a yogurt prepared from raw materials of the following parts by weight:

90-97 parts of raw milk, *Lactobacillus gasseri* of $(0.7-5)\times10^8$ CFU/100 g raw milk, *Streptococcus thermophilus* of $(0.1-9)\times10^{10}$ CFU/100 g raw milk, *Lactobacillus bulgaricus* of $(0.1-9)\times10^{10}$ CFU/100 g raw milk, *Lactobacillus acidophilus* of $(0.5-7)\times10^8$ CFU/100 g raw milk, *Lactobacillus plantarum* of $(0.5-7)\times10^8$ CFU/100 g raw milk, *Lactobacil-*

*lus paracasei* of $(0.1-9)\times10^7$ CFU/100 g raw milk, *Bifidobacterium breve* of $(1-5)\times10^6$ CFU/100 g raw milk, *Bifidobacterium lactis* of $(1-5)\times10^6$ CFU/100 g raw milk, *Bifidobacterium longum* of $(0.5-5)\times10^6$ CFU/100 g raw milk, 1-5 parts of inulin, 1-5 parts of fructooligosaccharides, 0.1-2 parts of galactooligosaccharides, 0.1-2 parts of polydextroses, 0.1-2 parts of isomaltooligosaccharides, and 0.1-0.6 parts of xylooligosaccharides.

In a possible implementation of the foregoing yogurt, the yogurt is prepared from the raw materials comprising the following parts by weight: 90-95 parts of raw milk, *Lactobacillus gasseri* of $(0.7-2)\times10^8$ CFU/100 g raw milk, *Streptococcus thermophilus* of $(0.5-2)\times10^{10}$ CFU/100 g raw milk, *Lactobacillus bulgaricus* of $(0.5-2)\times10^{10}$ CFU/100 g raw milk, *Lactobacillus acidophilus* of $(0.5-2)\times10^8$ CFU/100 g raw milk, *Lactobacillus plantarum* of $(0.5-2)\times10^8$ CFU/100 g raw milk, *Lactobacillus paracasei* of $(0.5-2)\times10^7$ CFU/100 g raw milk, *Bifidobacterium breve* of $(2-4)\times10^6$ CFU/100 g raw milk, *Bifidobacterium lactis* of $(2-4)\times10^6$ CFU/100 g raw milk, *Bifidobacterium longum* of $(0.5-2)\times10^6$ CFU/100 g raw milk, 2-3 parts of inulin, 2-3 parts of fructooligosaccharides, 0.6-0.8 parts of galactooligosaccharides, 0.4-0.5 parts of polydextroses, 0.2-0.3 parts of isomaltooligosaccharides, and 0.3-0.4 parts of xylooligosaccharides.

In a possible implementation of the foregoing yogurt, the yogurt is prepared from the raw materials comprising the following parts by weight: 90 parts of raw milk, *Lactobacillus gasseri* of $1\times10^8$ CFU/100 g raw milk, *Streptococcus thermophilus* of $1\times10^{10}$ CFU/100 g raw milk, *Lactobacillus bulgaricus* of $1\times10^{10}$ CFU/100 g raw milk, *Lactobacillus acidophilus* of $1\times10^8$ CFU/100 g raw milk, *Lactobacillus plantarum* of $1\times10^8$ CFU/100 g raw milk, *Lactobacillus paracasei* of $1\times10^7$ CFU/100 g raw milk, *Bifidobacterium breve* of $3\times10^6$ CFU/100 g raw milk, *Bifidobacterium lactis* of $3\times10^6$ CFU/100 g raw milk, *Bifidobacterium longum* of $1\times10^6$ CFU/100 g raw milk, 2 parts of inulin, 2 parts of fructooligosaccharides, 0.8 parts of galactooligosaccharides, 0.5 parts of polydextroses, 0.3 parts of isomaltooligosaccharides, and 0.4 parts of xylooligosaccharides.

In a possible implementation of the foregoing yogurt, the raw materials of the yogurt further comprise stevioside and mogroside, and the weight ratio of raw milk, stevioside and mogroside in the raw materials is 90-97:0.001-0.005:0.001-0.005.

In a possible implementation of the foregoing yogurt, the weight ratio of raw milk, stevioside and mogroside in the raw materials is 90:0.003:0.003.

The embodiments of this disclosure also provide a method for preparing the foregoing yogurt, comprising the following steps:

checking and filtering raw milk;

mixing inulin, fructooligosaccharides, galactooligosaccharides, polydextrose, isomaltooligosaccharides and xylooligosaccharides according to the above ratio;

preheating, homogenizing, sterilizing and cooling the obtained mixed raw materials;

inoculating *Lactobacillus gasseri* and compound bacteria according to the ratio, where the compound bacteria are a mixture of *Streptococcus thermophilus, Lactobacillus bulgaricus, Lactobacillus acidophilus, Lactobacillus plantarum, Lactobacillus paracasei, Bifidobacterium breve, Bifidobacterium lactis*, and *Bifidobacterium longum*; and fermentating, cooling, preparing for filling, filling, refrigerating and post-maturating.

In a possible implementation of the foregoing method, when mixing inulin, fructooligosaccharides, galactooligosaccharides, polydextrose, isomaltooligosaccharide and xylooligosaccharide, stevioside and mogroside are also added according to the ratio.

In a possible implementation of the foregoing method, the conditions for preheating, homogenizing, sterilizing and cooling the obtained mixed raw materials are: preheating the obtained mixed raw materials to 60-65° C., homogenizing at 100-200 bar, sterilizing at 95±2° C. for 5 min, and then cooling to 43±2° C.

In a possible implementation of the foregoing method, the conditions for fermenting are: fermenting at 42±2° C., and terminating fermentation when the fermentation acidity is greater than or equal to 70° T (pH<4.60).

The embodiments of this disclosure also provide use of the foregoing yogurt in preparation of a food, a health product, and a medicine for preventing overweight and/or obese pregnant women from constipation and gestational diabetes during the gestation period.

Inulin: control blood lipids; lower blood sugar; promote absorption of minerals, regulate intestinal microflora, increase bifidobacteria and lactobacilli, improve intestinal health, prevent constipation; inhibit the production of toxic fermentation products, protect the liver, prevent colon cancer, and the like.

Fructooligosaccharides: have low calorie value, prevent dental caries, proliferation of bifidobacteria and *Lactobacillus plantarum*, lower cholesterol and triglycerides in serum, prevent diarrhea and constipation, and the like.

Galactooligosaccharides: *Bifidobacterium, Lactobacillus acidophilus* and other beneficial bacteria in the human intestinal tract that are an excellent source of nutrition and an effective proliferation factor, can improve the digestion and absorption function of the human intestinal tract.

Polydextroses: regulate lipid metabolism, lower cholesterol, reduce sugar absorption, prevent and treat constipation, and the like.

Isomaltooligosaccharides: prevent caries, proliferation of *Bifidobacterium breve*, and the like.

Xylooligosaccharides: reduce the production of toxic fermentation products and harmful bacterial enzymes, inhibit pathogenic bacteria and diarrhea, prevent constipation, protect liver functions, lower serum cholesterol, lower blood pressure, enhance immunity, prevent cancer and the like. The xylooligosaccharides have obvious proliferation effect on *Bifidobacterium adolescentis, Bifidobacterium breve* and *Bifidobacterium bifidum*.

Stevioside: low calorie value, high safety and high stability; and a natural low-calorie sweetener. Stevioside has a calorific value of only ⅓₀₀ of that of sucrose. After being ingested by human body, it is not absorbed by the human body and does not generate heat. It is a sweetener suitable for patients with diabetes and obesity.

Mogroside: prevent caries, have a sweetness 300 times higher than sucrose and zero calorie, and effects of clearing away heat, moistening the lungs, relieving cough, moistening the intestines and relaxing the bowels, and a preventive effect on obesity, constipation, diabetes, and the like

Beneficial Effects

1. The yogurt provided by the embodiment of this disclosure adopts a compound formula that in addition to the traditional lactic acid bacteria (*Lactobacillus bulgaricus*, and *Streptococcus thermophilus*), has various probiotics, including *Lactobacillus gasseri, Lactobacillus acidophilus, Lactobacillus plantarum, Lactobacillus paracasei, Bifidobacterium breve, Bifidobacterium lactis*, and *Bifidobacterium longum*, and also prebiotics and dietary fibers to improve intestinal health. The intestinal health is inextricably linked to probiotics and prebiotics. The effects of probiotics and prebiotics are not independent of each other. When they are used together, the effect on intestinal health is better than that of probiotics or prebiotics alone. This is because of the synergistic effects between live probiotics and specific selective substrates, that is, prebiotics. Prebiotics, as food for probiotics in the intestinal tract, cannot be used by harmful bacteria, but may promote the growth and proliferation of beneficial bacteria and inhibit the growth of harmful bacteria. Probiotics and prebiotics complement each other and work together to keep the balance of the intestinal microecology, prevent and improve constipation and diarrhea, improve immunity, and maintain human health.

The yogurt provided by the embodiment of this disclosure may prevent constipation and gestational diabetes in overweight and/or obese pregnant women during the gestation period, and may help improve maternal glucose and lipid metabolism and insulin resistance by regulating the intestinal microecology of overweight and/or obese pregnant women, reduce the risk of gestational diabetes, thereby creating a good intrauterine environment, reducing the risk of fetal-derived adult diseases, and improving the quality of the birth population.

2. The yogurt provided by the embodiment of this disclosure adopts raw milk with high protein content, the protein in the finished yogurt is 39% higher than the national minimum standard of flavored yogurt, and per 200 ml of the yogurt provided by the embodiments of this disclosure contains 12 g of soluble dietary fibers, which is 48% of the dietary fiber nutrient reference value specified in GB28050 National Food Safety Standard for Nutrition Labeling of Prepackaged Foods (recommended intake of 25 g/day).

BRIEF DESCRIPTION OF THE DRAWINGS

One or more embodiments are exemplified by the figures in the corresponding drawings, and these exemplified descriptions do not constitute limitations on the embodiments. The word "exemplary" is used exclusively herein to mean "serving as an example, an embodiment, or an illustration." Any embodiment described herein as "exemplary" is not necessarily to be construed as preferred or advantageous over other embodiments.

DETAILED DESCRIPTION OF THE INVENTION

Figure 1:
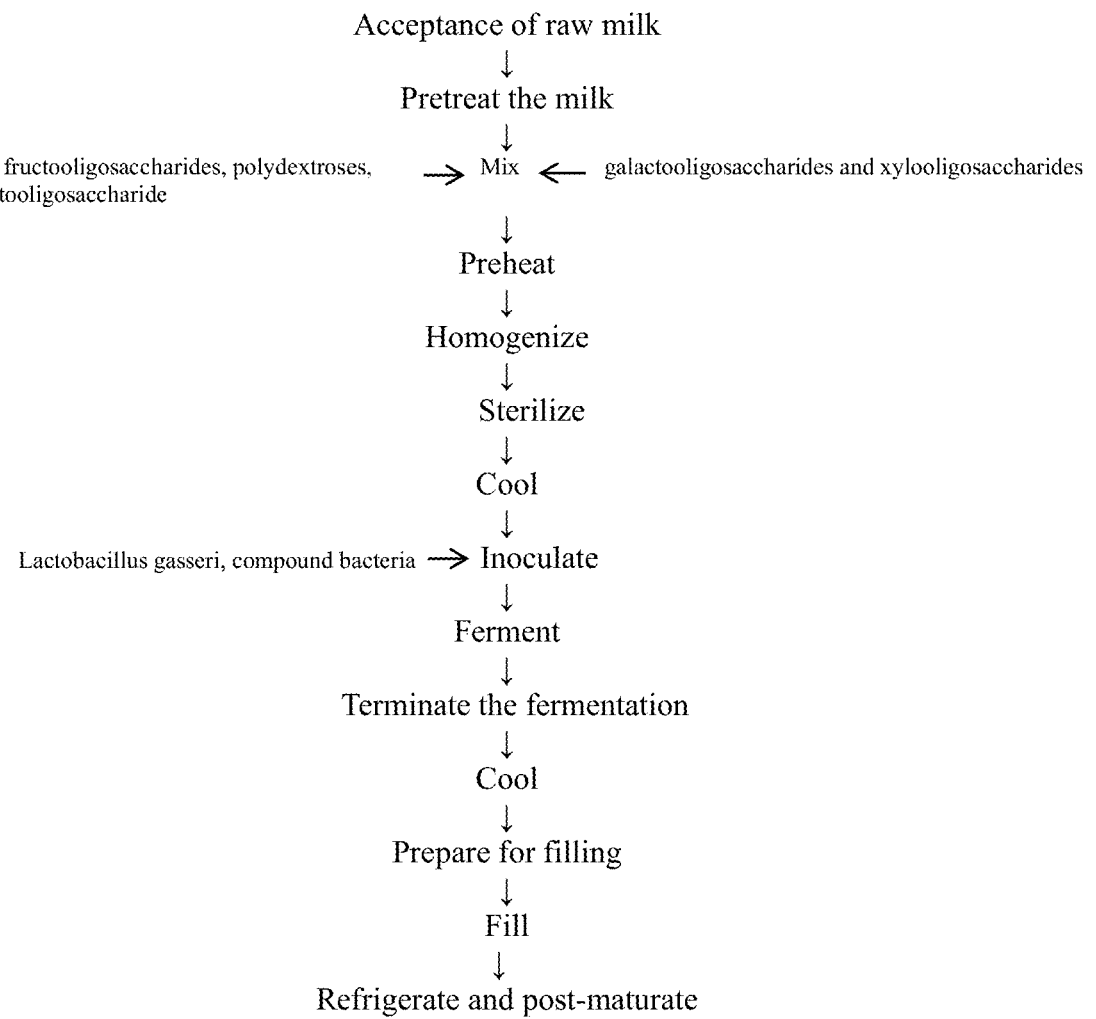
FIG. 1 is a process flow diagram of a method for preparing yogurt in an embodiment of this disclosure.

In order to make the objectives, technical solutions, and advantages of the embodiments of this disclosure clearer, the technical solutions in the embodiments of this disclosure will be described clearly and completely below. It is apparent that the described embodiments are part of the embodiments of this disclosure, but not exhaustive. Based on the embodiments of this disclosure, all other embodiments obtained by those of ordinary skill in the art without creative work shall fall within the protection scope of this disclosure.

In addition, in order to better illustrate this disclosure, numerous specific details are given in the following specific embodiments. Those skilled in the art should understand that this disclosure may also be implemented without certain specific details. In some embodiments, the raw materials, elements, methods, means, or the like that are well known to those skilled in the art are not described in detail in order to highlight the gist of this disclosure.

Unless otherwise expressly stated, throughout the specification and claims, the term "comprising" or a variation thereof such as "including" or "contain" is construed as including the stated element or component, without excluding other elements or other components.

In the following examples, *Streptococcus thermophilus, Lactobacillus bulgaricus, Lactobacillus paracasei, Bifidobacterium breve*, and *Bifidobacterium lactis* used are all commercially available products. *Lactobacillus gasseri, Lactobacillus plantarum, Lactobacillus acidophilus*, and *Bifidobacterium longum* are self-owned strains by Beijing Sanyuan Foods Co., LTd, and have all been preserved in the China General Microorganism Culture Collection and Management Center before the application date, among which:

*Lactobacillus gasseri* is *Lactobacillus gasseri* B1-26 derived from breast milk, which was preserved on Apr. 27, 2020 in China General Microbiological Culture Collection Center (No. 3, No. 1 Beichen West Road, Chaoyang District, Beijing, China) with a preservation number of CGMCC No. 19749, and has strong adhesion ability and advantages in acid resistance, bile salt resistance, and bacteria inhibition;

*Lactobacillus plantarum* is *Lactobacillus plantarum* R9 derived from breast milk, which was preserved on Apr. 27, 2020 in China General Microbiological Culture Collection Center (No. 3, No. 1 Beichen West Road, Chaoyang District, Beijing, China) with a preservation number of CGMCC No. 19748. The *Lactobacillus plantarum* derived from breast milk has an adhesion rate to intestinal cells of over 140%, where the adhesion of the *Lactobacillus* to epithelial cells is the underlying basis for its probiotic function. The adhered *Lactobacillus* may be present in the intestinal tract and may resist the invasion of pathogenic bacteria, producing metabolites such as antimicrobial peptides to help effectively kill pathogenic bacteria, so as to avoid the infection of the intestinal tract by pathogenic bacteria. The *Lactobacillus plantarum* derived from breast milk has a inhibitory effect against 8 common pathogenic bacteria (*Listeria monocytogenes, Staphylococcus aureus, Bacillus cereus, Escherichia coli, Shigella soong, Salmonella typhi, Enterobacter sakazakii*, and *Salmonella enteritidis*), with a diameter of inhibition zone of ≥20 mm, and in particular has a better inhibitory effect on *Escherichia coli*, with a diameter of the inhibition zone of ≥28.5 mm. The *Lactobacillus plantarum* derived from breast milk has a survival rate of ≥107% in 3 hours at a pH of 2.5, and a survival rate of ≥115% after 6 hours, and a survival rate of ≥225% after 1 hour at 0.3% bile salt.

*Lactobacillus acidophilus* is the strain SY02 protected by the patent ZL200410000767.0, which was preserved on Jan. 6, 2004 in China General Microbiological Culture Collection Center (No. 3, No. 1 Beichen West Road, Chaoyang District, Beijing, China) with a preservation number of CGMCC No. 1084, and has advantages in acid resistance, bile salt resistance, and bacteria inhibition; *Bifidobacterium*

*longum* is the strain SY31 protected by the patent ZL200410000768.5, which was preserved on Jan. 6, 2004 in China General Microbiological Culture Collection Center (No. 3, No. 1 Beichen West Road, Chaoyang District, Beijing, China) with a preservation number of CGMCC No. 1085, and has advantages in acid resistance, bile salt resistance, and bacteria inhibition.

Example 1

A yoghurt for regulating intestinal tract was prepared from the raw materials of the following parts by weight:

90 parts of raw milk, *Lactobacillus gasseri* of $1\times10^8$ CFU/100 g raw milk, *Streptococcus thermophilus* of $1\times10^{10}$ CFU/100 g raw milk, *Lactobacillus bulgaricus* of $1\times10^{10}$ CFU/100 g raw milk, *Lactobacillus acidophilus* of $1\times10^8$ CFU/100 g raw milk, *Lactobacillus plantarum* of $1\times10^8$ CFU/100 g raw milk, *Lactobacillus paracasei* with $1\times10^7$ CFU/100 g raw milk, *Bifidobacterium breve* of $3\times10^6$ CFU/100 g raw milk, *Bifidobacterium lactis* of $3\times10^6$ CFU/100 g raw milk, *Bifidobacterium longum* of $1\times10^6$ CFU/100 g raw milk, 2 parts of inulin, 2 parts of fructooligosaccharides, 0.8 parts of galactooligosaccharides, 0.5 parts of polydextroses, 0.3 parts of isomaltooligosaccharides, 0.4 parts of xylooligosaccharides, 0.003 parts of stevioside and 0.003 parts of mogroside.

A yoghurt that regulates intestinal tract was prepared by using the foregoing raw materials through the following steps:

checking and filtering raw milk;

dry mixing inulin, fructooligosaccharides, polydextrose, and isomaltooligosaccharides (inulin, fructooligosaccharides, polydextrose, and isomaltooligosaccharides are all in powder form) according to the ratio, and slowly pouring them into a mixer to thoroughly mix with the raw milk, and then pouring the galactooligosaccharides and xylooligosaccharides (galactooligosaccharides and xylooligosaccharides are both liquid) into the mixer to fully mix with the raw milk;

preheating the obtained mixed raw materials to 60-65° C., homogenizing at 100-200 bar, sterilizing at 95±2° C. for 5 min, and then cooling to 43±2° C.;

inoculating *Lactobacillus gasseri* and compound bacteria according to the ratio, the compound bacteria are mixture of *Streptococcus thermophilus, Lactobacillus bulgaricus, Lactobacillus acidophilus, Lactobacillus plantarum, Lactobacillus paracasei, Bifidobacterium breve, Bifidobacterium lactis*, and *Bifidobacterium longum*; and fermenting at 42±2° C., and terminating the fermentation when the fermentation acidity is greater than or equal to 70° T (pH<4.60);

cooling, preparing for filling, filling, refrigerating and post-maturating, to obtain the yogurt for regulating intestinal microecology. The cooling, preparing for filling, filling, refrigerating and post-maturating may be carried out on conditions according to the prior art.

Example 2

A yoghurt for regulating intestinal microecology was prepared from the raw materials of the following parts by weight:

90 parts of raw milk, *Lactobacillus gasseri* of $1\times10^8$ CFU/100 g raw milk, *Streptococcus thermophilus* of $1\times10^{10}$ CFU/100 g raw milk, *Lactobacillus bulgaricus*

7      8 of $1\times10^{10}$ CFU/100 g raw milk, *Lactobacillus acidophilus* of $1\times10^8$ CFU/100 g raw milk, *Lactobacillus plantarum* of $1\times10^8$ CFU/100 g raw milk, *Lactobacillus paracasei* of $1\times10^7$ CFU/100 g raw milk, *Bifidobacterium breve* of $3\times10^6$ CFU/100 g raw milk, *Bifidobacterium lactis* of $3\times10^6$ CFU/100 g raw milk, *Bifidobacterium longum* of $1\times10^6$ CFU/100 g raw milk, 2 parts of inulin, 2 parts of fructooligosaccharides, 0.6 parts of galactooligosaccharides, 0.4 parts of polydextroses, 0.2 parts of isomaltooligosaccharides, 0.3 parts of xylooligosaccharides, 0.005 parts of stevioside and 0.005 parts of mogroside.

A yoghurt that regulates intestinal microecology was prepared by using the foregoing raw materials through the following steps:

checking and filtering raw milk;

dry mixing inulin, fructooligosaccharides, polydextrose, and isomaltooligosaccharides (inulin, fructooligosaccharides, polydextrose, and isomaltooligosaccharides are all in powder form) according to the ratio, and slowly pouring them into a mixer to thoroughly mix with the raw milk, and then pouring the galactooligosaccharides and xylooligosaccharides (galactooligosaccharides and xylooligosaccharides are both liquid) into the mixer to fully mix with the raw milk;

preheating the obtained mixed raw materials to 60-65° C., homogenizing at 100-200 bar, sterilizing at 95±2° C. for 5 min, and then cooling to 43±2° C.;

inoculating *Lactobacillus gasseri* and compound bacteria according to the ratio, where the compound bacteria refer to a mixture of *Streptococcus thermophilus, Lactobacillus bulgaricus, Lactobacillus acidophilus, Lactobacillus plantarum, Lactobacillus paracasei, Bifidobacterium breve, Bifidobacterium lactis*, and *Bifidobacterium longum*; and fermenting at 42±2° C., and terminating the fermentation when the fermentation acidity is greater than or equal to 70° T (pH<4.60);

cooling, preparing for filling, filling, refrigerating and post-maturating, to obtain the yogurt for regulating intestinal microecology.

Example 3

A yoghurt for regulating intestinal microecology was prepared from the raw materials of the following parts by weight:

95 parts of raw milk, *Lactobacillus gasseri* of $2\times10^8$ CFU/100 g raw milk, *Streptococcus thermophilus* of $2\times10^{10}$ CFU/100 g raw milk, *Lactobacillus bulgaricus* of $2\times10^{10}$ CFU/100 g raw milk, *Lactobacillus acidophilus* of $2\times10^8$ CFU/100 g raw milk, *Lactobacillus plantarum* of $0.5\times10^8$ CFU/100 g raw milk, *Lactobacillus paracasei* of $0.5\times10^7$ CFU/100 g raw milk, *Bifidobacterium breve* of $2\times10^6$ CFU/100 g raw milk, *Bifidobacterium lactis* of $2\times10^6$ CFU/100 g raw milk, *Bifidobacterium longum* of $0.5\times10^6$ CFU/100 g raw milk, 2 parts of inulin, 2 parts of fructooligosaccharides, 0.8 parts of galactooligosaccharides, 0.5 parts of polydextroses, 0.3 parts of isomaltooligosaccharides, 0.4 parts of xylooligosaccharides, 0.003 parts of stevioside and 0.003 parts of mogroside.

A yoghurt that regulates intestinal microecology was prepared by using the foregoing raw materials through the following steps:

checking and filtering raw milk;

dry mixing inulin, fructooligosaccharides, polydextrose, and isomaltooligosaccharides (inulin, fructooligosaccharides, polydextrose, and isomaltooligosaccharides are all in powder form) according to the ratio, and slowly pouring them into a mixer to thoroughly mix with the raw milk, and then pouring the galactooligosaccharides and xylooligosaccharides (galactooligosaccharides and xylooligosaccharides are both liquid) into the mixer to fully mix with the raw milk;

preheating the obtained mixed raw materials to 60-65° C., homogenizing at 100-200 bar, sterilizing at 95±2° C. for 5 min, and then cooling to 43±2° C.;

inoculating *Lactobacillus gasseri* and compound bacteria according to the ratio, where the compound bacteria are mixture of *Streptococcus thermophilus, Lactobacillus bulgaricus, Lactobacillus acidophilus, Lactobacillus plantarum, Lactobacillus paracasei, Bifidobacterium breve, Bifidobacterium lactis*, and *Bifidobacterium longum*; and fermenting at 42±2° C., and terminating the fermentation when the fermentation acidity is greater than or equal to 70° T (pH<4.60);

cooling, preparing for filling, filling, refrigerating and post-maturating, to obtain the yogurt for regulating intestinal microecology.

Test Example 1: Prevention of Constipation and Gestational Diabetes in Overweight/Obese Pregnant Women 1. Subjects Inclusion criteria: pregnant women who have lived in Beijing for at least 5 years; age 18-35 years; singleton pregnancy; gestational age 8-12 weeks$^{+6}$ (based on the last menstrual period or ultrasonography monitoring); BMI ≥25 kg/m$^2$; no history of hypertension, diabetes, hyperlipidemia, hepatitis, nephritis, digestive tract diseases (chronic gastritis, enteritis, gastric ulcer and duodenal ulcer, and the like) and infectious diseases (hepatitis, tuberculosis, and the like) before the intervention.

Exclusion criteria: the following must not be included in this study: took antibiotics, probiotics or prebiotics in the past 1 month, smoke or drink regularly, conceive through assisted reproductive technology, cannot answer the questions correctly due to mental illnesses or were unwilling to conduct questionnaires; have history of bariatric surgery; unability to follow dietary recommendations; or have lactose intolerance or milk protein allergy.

2. Study Content

Pregnant women were enrolled at 8.99±1.49 W of gestational age, 163.24±5.91 cm in height, 75.0±10.6 kg in pre-pregnancy weight, and 75.4±10.2 kg in weight at the time of enrollment, which was in line with the indicators of overweight and obese pregnant women. A constipation scale was filled out at the time of enrollment to obtain baseline data. A randomized controlled trial (RCT) study was used to conduct computer randomization. The enrolled overweight/obese pregnant women were divided into yogurt intervention group (N=77) and routine control group (N=128). There were no significant differences in gestational age, height, and weight between the two groups of pregnant women. The study started at 13 weeks of gestation and was followed up to 42 days postpartum.

Routine control group: According to the dietary guidelines for pregnant and lying-in women formulated by the Chinese Society of Maternal and Child Nutrition and the recommendations of the Diet Pagoda, trained nutritionists gave guidance on diet, exercise and weight gain during pregnancy (in the form of group education), followed by routine obstetric examination, with no intervention.

Yoghurt intervention group: According to the dietary guidelines for pregnant and lying-in women formulated by the Chinese Society of Maternal and Child Nutrition and the recommendations of the Diet Pagoda, trained nutritionists gave guidance on diet, exercise and weight gain during pregnancy (in the form of group education), and 200 ml of yoghurt (obtained in Example 1) was ingested with a snack daily since the 13th week of pregnancy.

3. Research Methods and Effectiveness Evaluation

The PAC-SYM constipation scale was used to analyze constipation, which was quantified from stool properties (hard stools, decreased stool volume), rectal symptoms (reduced bowel movements, laborious defecation, painful defecation, difficulty in defecation while desiring to defecate, rectal bleeding or tearing, rectal burning sensation) and other aspects, where "none" scored 0 points, "mild" scored 1 point, "moderate" scored 2 points, "severe" scored 3 points, and "very severe" scored 4 points.

The results showed that there was a significant difference between the routine control group and the yogurt intervention group in the scores of fecal volume indicators ($P=0.01$). With the increase of gestational weeks, the weight of pregnant women showed an increasing trend. More people in the routine control group had a decrease in fecal volume, but in the yogurt intervention group, due to the intervention of yogurt, not only did the number of people with decreased fecal volume not increase, but there was also an upward trend in the number of people with more feces. Although there was no significant difference between the routine control group and the yogurt intervention group in other constipation symptom indicators such as hard stools, decreased frequency of defecation, laborious defecation, painful defecation, difficulty in defecation while desiring to defecate, rectal bleeding or tearing, rectal burning sensation, the foregoing conditions in the yogurt intervention group showed a slight downward trend as a whole. It fully showed that the intervention of fermented milk during pregnancy may effectively prevent constipation symptoms that occur with the increase of pregnancy.

In addition to improving the symptoms of constipation during pregnancy, the intake of yogurt in the embodiments of this disclosure may significantly reduce the incidence of gestational diabetes. Compared with the routine control group with an incidence of gestational diabetes of 32%, and the yogurt intervention group had an incidence of gestational diabetes of only 22%, indicating a significant difference between the two groups.

Test Example 2

The yogurt prepared in Example 1, Example 2, and Example 3 was subjected to sensory evaluation, which was conducted by an evaluation team consisted of 20 laboratory personnel of our institute, the specific evaluation indexes are tissue state, taste and smell, color, viscosity, sweet and sour ratio, and the evaluation criteria are as follows:

tissue state (1-10 points, the higher the score, the better the smoothness and fineness of the organization state);

taste and smell (1-10 points, the higher the score, the better the overall flavor);

color (1-10 points, the higher the score, the better the milky whiteness and luster);

viscosity (1 refers to too thin, 5 refers to suitable, and 10 refers to too thick); and sweet and sour ratio (1 refers to too sweet, 5 refers to suitable, and 10 refers to too sour).

Figure 2:
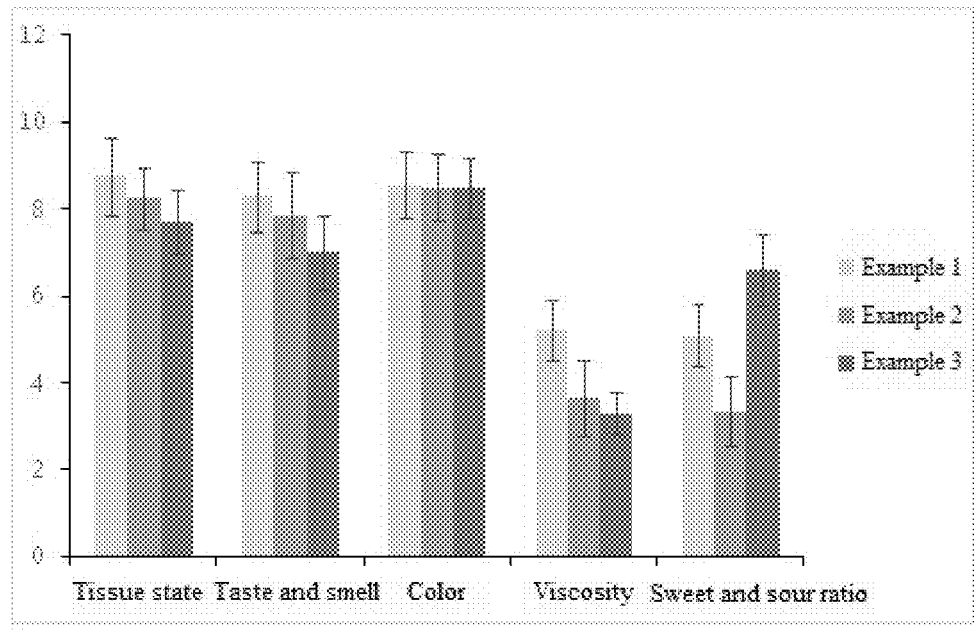
FIG. 2 is a sensory evaluation comparison of the yogurt obtained in Example 1, Example 2 and Example 3.

The results are shown in FIG. 2, the tissue state, taste and smell of Example 1 were better than those of Example 2 and Example 3, indicating that the tissue state of Example 1 was more delicate and the overall flavor was better; the color of Example 1, Example 2 and Example 3 was comparable, they all had good color; and in terms of viscosity, that in Example 1 was better than Example 2 and Example 3; and the sweet and sour ratio in Example 1 was suitable, in Example 2 was sweeter, and in Example 3 was more sour. The evaluation team overall preferred Example 1.

Finally, it should be noted that: the above embodiments are only used to illustrate the technical solutions of this disclosure, but not to limit thereto. Although this disclosure has been described in detail with reference to the foregoing embodiments, those of ordinary skill in the art should understand modifications made to the technical solutions described in the foregoing embodiments, or equivalent replacements of some technical features thereof are possible, without making the essence of the corresponding technical solutions depart from the spirit and scope of the technical solutions of the embodiments of this disclosure.

INDUSTRIAL APPLICABILITY

The yoghurt provided by the embodiments of this disclosure is prepared from the raw materials comprising the following parts by weight: 90-97 parts of raw milk, *Lactobacillus gasseri* of $(0.7-5)\times10^8$ CFU/100 g raw milk, *Streptococcus thermophilus* of $(0.1-9)\times10^{10}$ CFU/100 g raw milk, *Lactobacillus bulgaricus* of $(0.1-9)\times10^{10}$ CFU/100 g raw milk, *Lactobacillus acidophilus* of $(0.5-7)\times10^8$ CFU/100 g raw milk, *Lactobacillus plantarum* of $(0.5-7)\times10^8$ CFU/100 g raw milk, *Lactobacillus paracasei* of $(0.1-9)\times10^7$ CFU/100 g raw milk, *Bifidobacterium breve* of $(1-5)\times10^6$ CFU/100 g raw milk, *Bifidobacterium lactis* of $(1-5)\times10^6$ CFU/100 g raw milk, *Bifidobacterium longum* of $(0.5-5)\times10^6$ CFU/100 g raw milk, 1-5 parts of inulin, 1-5 parts of fructooligosaccharides, 0.1-2 parts of galactooligosaccharides, 0.1-2 parts of polydextroses, 0.1-2 parts of isomaltooligosaccharides, and 0.1-0.6 parts of xylooligosaccharides. A compound formula is used, which in addition to the traditional lactic acid bacteria (*Lactobacillus bulgaricus*, and *Streptococcus thermophilus*), comprises various probiotics, including *Lactobacillus gasseri*, *Lactobacillus acidophilus*, *Lactobacillus plantarum*, *Lactobacillus paracasei*, *Bifidobacterium breve*, *Bifidobacterium lactis*, and *Bifidobacterium longum*, and also prebiotics and dietary fibers to improve intestinal health. The yogurt provided by the embodiment of this disclosure may prevent constipation and gestational diabetes in overweight and/or obese pregnant women during the gestation period, and may help improve maternal glucose and lipid metabolism and insulin resistance by regulating the intestinal microecology of overweight and/or obese pregnant women, reduce the risk of gestational diabetes, thereby creating a good intrauterine environment, reducing the risk of fetal-derived adult diseases, and improving the quality of the birth population.

The invention claimed is:

1. A yoghurt comprising consisting of raw materials in following parts by weight:

90 parts of raw milk, *Lactobacillus gasseri* of $1\times10^8$ CFU/100 g raw milk, *Streptococcus thermophilus* of $1\times10^{10}$ CFU/100 g raw milk, *Lactobacillus bulgaricus* of $1\times10^{10}$ CFU/100 g raw milk, *Lactobacillus acidophilus* of $1\times10^8$ CFU/100 g raw milk, *Lactobacillus plantarum* of $1\times10^8$ CFU/100 g raw milk, *Lactobacillus paracasei* of $1\times10^7$ CFU/100 g raw milk, *Bifidobacterium breve* of $3\times10^6$ CFU/100 g raw milk, *Bifidobacterium lactis* of $3\times10^6$ CFU/100 g raw milk, *Bifidobacterium longum* of $1\times10^6$ CFU/100 g raw milk, 2 parts of inulin, 2 parts of fructooligosaccharides, 0.8 parts of galactooligosaccharides, 0.5 parts of polydextroses, 0.3 parts of isomaltooligosaccharides, and 0.4 parts of xylooligosaccharides, 0.003 parts of stevioside, and 0.003 parts of mogroside;

wherein the *Lactobacillus gasseri* is *Lactobacillus gasseri* B1-26 derived from breast milk, which was preserved on Apr. 27, 2020 in China General Microbiological Culture Collection Center with a preservation number of CGMCC No. 19749;

the *Lactobacillus plantarum* is *Lactobacillus plantarum* R9 derived from breast milk, which was preserved on Apr. 27, 2020 in China General Microbiological Culture Collection Center with a preservation number of CGMCC No. 19748;

the *Lactobacillus acidophilus* is the strain SY02 which was preserved on Jan. 6, 2004 in China General Microbiological Culture Collection Center with a preservation number of CGMCC No. 1084; and the *Bifidobacterium longum* is the strain SY31 which was preserved on Jan. 6, 2004 in China General Microbiological Culture Collection Center with a preservation number of CGMCC No. 1085.

2. A method for preventing overweight and/or obese pregnant women from constipation and gestational diabetes during the gestation period, comprising administration of the yogurt according to claim 1 to the pregnant women.

* * * * *